(12) United States Patent
St. Laurent et al.

(10) Patent No.: US 9,242,923 B2
(45) Date of Patent: Jan. 26, 2016

(54) COMPOSITONS AND METHODS

(75) Inventors: Joseph P. St. Laurent, Lakeville, MA (US); Scott A. Goodrich, Stoughton, MA (US); Gerald S. Jones, Jr., Norwood, MA (US)

(73) Assignee: CHEMIC LABORATORIES INC., Canton, MA (US)

( * ) Notice: Subject to any disclaimer, the term of this patent is extended or adjusted under 35 U.S.C. 154(b) by 197 days.

(21) Appl. No.: 13/634,170

(22) PCT Filed: Mar. 11, 2011

(86) PCT No.: PCT/US2011/028196
§ 371 (c)(1),
(2), (4) Date: Dec. 21, 2012

(87) PCT Pub. No.: WO2011/112997
PCT Pub. Date: Sep. 15, 2011

(65) Prior Publication Data
US 2013/0096192 A1     Apr. 18, 2013

Related U.S. Application Data

(60) Provisional application No. 61/313,076, filed on Mar. 11, 2010.

(51) Int. Cl.
*A61K 9/00* (2006.01)
*C07C 69/14* (2006.01)
*A61K 9/06* (2006.01)
*A61K 31/22* (2006.01)
*C07C 69/68* (2006.01)

(52) U.S. Cl.
CPC .............. *C07C 69/14* (2013.01); *A61K 9/0014* (2013.01); *A61K 9/06* (2013.01); *A61K 31/22* (2013.01); *C07C 69/68* (2013.01)

(58) Field of Classification Search
CPC .................................................... A61K 9/0014
See application file for complete search history.

(56) References Cited

U.S. PATENT DOCUMENTS

| 4,874,794 A | 10/1989 | Katz |
| 5,331,012 A * | 7/1994 | Riddick et al. ................ 514/626 |
| 7,030,203 B2 | 4/2006 | Mosbey et al. |
| 2004/0033982 A1 | 2/2004 | Katz et al. |
| 2005/0287179 A1 | 12/2005 | Muse et al. |
| 2006/0084154 A1 | 4/2006 | Jones et al. |
| 2006/0229364 A1 * | 10/2006 | Hobbs et al. .................. 514/547 |
| 2007/0082039 A1 | 4/2007 | Jones et al. |

FOREIGN PATENT DOCUMENTS

| EP | 1557167 A1 | 7/2005 |
| WO | 03032915 A2 | 4/2003 |

OTHER PUBLICATIONS

Razonable RR. Antiviral drugs for viruses other than human immunodeficiency virus. Mayo Clin Proc. Oct. 2011;86(10):1009-26.*
Herpecin-L product page, www.herpecin.com/about.html (2013).*
CID 20514171. "PubChem Public Chemical Database." Dec. 5, 2007; compound of formula in p. 1.
International Search Report for PCT/US2011/028196 dated May 3, 2011.
Preliminary Report on Patentability for PCT/US2011/028196 dated Sep. 11, 2012.
Written Opinion for PCT/US2011/028196 dated May 3, 2011.

* cited by examiner

*Primary Examiner* — Paul Zarek
(74) *Attorney, Agent, or Firm* — Lando & Anastasi LLP

(57) ABSTRACT

Described herein are compositions (e.g., a pharmaceutical composition) and compounds of formula I, and their use in the treatment and/or prevention of diseases and disorders.

3 Claims, No Drawings

US 9,242,923 B2

COMPOSITONS AND METHODS

CLAIM OF PRIORITY

This application claims priority under 35 U.S.C. §371 PCT Application No.: PCT/US2011/028196, filed Mar. 11, 2011, published as WO 2011/112997 on Sep. 15, 2011, which claims priority to U.S. Ser. No. 61/313,076, filed Mar. 11, 2010, the contents of each of which is hereby incorporated by reference in its entirety.

TECHNICAL FIELD OF THE INVENTION

The invention relates to saturated fatty alcohol esters of hydroxycarboxylic acids, their compositions and methods of treating or preventing infections (e.g., viral infections). The invention also relates to methods of making high-purity fatty alcohol esters of hydroxycarboxylic acids in scalable (e.g., multi-kilogram scale) batches.

BACKGROUND OF THE INVENTION

Antiviral activities in saturated alcohols were identified 30 years ago. Activities have been observed for $C_{10}$-$C_{12}$ alcohols including cytotoxic and hemolytic effects. In addition, antiviral activity has been observed for $C_{20}$-$C_{26}$ alcohols (See e.g., U.S. Pat. No. 4,874,794; International Publication No. WO 03/032915; U.S. Publication No. US2004/0033982; and EP Patent No. 1557167. An example of one of the antiviral alcohols is 1-docosanol, the active ingredient in the FDA-approved OTC treatment for cold sores, Abreva®.

Cold sores (i.e., recurrent herpes simplex labialis (HSL)) are recurrent infections caused by herpes simplex virus 1 (HSV-1). 1-Docosanol (behenyl alcohol) is a $C_{22}$ primary alcohol that inhibits HSV replication in tissue culture. It blocks one or more steps of viral entry, perhaps predominantly interfering with viral fusion with the host cell. The spectrum of antiviral activity of docosanol is not limited to HSV-1, and includes HSV-2, VZV, HCMV, HIV-1, respiratory syncytial virus, and influenza A. The mechanism of antiviral action in this class of compounds has not yet been fully delineated.

Antiviral activity has also been documented for certain fatty alcohol esters of hydroxycarboxylic acids (See e.g., U.S. Publication No. US2006/0229364 (2006)). Accordingly, topical antiviral activity can be expected by the application of a $C_7$-$C_{14}$ saturated fatty alcohol ester of a $C_2$-$C_8$ hydroxycarboxylic acid, e.g., lauryl ($C_{12}$) lactate or myristyl ($C_{14}$) lactate, either alone or in combination with another antiviral component.

SUMMARY OF INVENTION

In one aspect, the present invention is directed to a composition (e.g., a pharmaceutical composition) comprising a compound of formula (I):

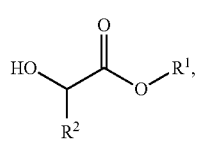

(I)

wherein
$R^1$ is a $C_{15-40}$ alkyl; and
$R^2$ is hydrogen, alkyl, aryl, heteroaryl, heterocyclyl or aralkyl.

In certain embodiments, $R^1$ is a $C_{15-26}$ alkyl group. In some embodiments, $R^1$ is a $C_{20-26}$ alkyl group. In some embodiments, $R^1$ is a $C_{20-22}$ alkyl group. In some embodiments, $R^1$ is a $C_{22}$ alkyl group.

In certain embodiments, $R^2$ is alkyl (e.g., $C_{1-4}$ alkyl). In certain embodiments, $R^2$ is $C_{1-4}$ alkyl (e.g., methyl). In certain embodiments, $R^2$ is aryl (e.g., phenyl). In some embodiments, $R^2$ is aralkyl (e.g., benzyl).

In certain embodiments, the composition is an anti-viral composition. In some embodiments, the compound of formula (I) is an anti-viral compound.

In certain embodiments, the composition is substantially free of long chain ($C_{20}$-$C_{28}$) aliphatic alcohols (e.g., behenyl alcohol). In some embodiments, the composition is substantially free of Zovirax® (acyclovir). In some embodiments, the composition is substantially free of Denavir® (penciclovir). In some embodiments, the composition is substantially free of a second anti-viral compound (e.g., a viral entry inhibitor, a reverse transcriptase inhibitor, an integrase inhibitor, a transcription inhibitor, or a protease inhibitor).

In certain embodiments, at least 50% by weight of the composition is a compound of formula (I). In some embodiments, at least 75% by weight of the composition is a compound of formula (I). In some embodiments, at least 85% by weight of the composition is a compound of formula (I). In some embodiments, at least 90% by weight of the composition is a compound of formula (I). In some embodiments, at least 95% by weight of the composition is a compound of formula (I). In some embodiments, at least 97% by weight of the composition is a compound of formula (I). In some embodiments, the composition consists essentially of a compound of formula (I).

In certain embodiments, the composition comprises a racemic mixture of the compound of formula (I) (e.g., less than 10% enantiomeric excess of either the R or S stereoisomer). In certain embodiments, the composition comprises at least 10% enantiomeric excess of the R stereoisomer of the compound of formula (I). In certain embodiments, the composition comprises at least 50% enantiomeric excess of the R stereoisomer of the compound of formula (I). In some embodiments, the composition comprises at least 75% enantiomeric excess of the R stereoisomer of the compound of formula (I). In some embodiments, the composition comprises at least 85% enantiomeric excess of the R stereoisomer of the compound of formula (I). In some embodiments, the composition comprises at least 90% enantiomeric excess of the R stereoisomer of the compound of formula (I). In some embodiments, the composition comprises at least 95% enantiomeric excess of the R stereoisomer of the compound of formula (I). In some embodiments, the composition comprises at least 97% enantiomeric excess of the R stereoisomer of the compound of formula (I). In some embodiments, the composition comprises at least 99% enantiomeric excess of the R stereoisomer of the compound of formula (I).

In certain embodiments, the composition comprises at least 10% enantiomeric excess of the S stereoisomer of the compound of formula (I). In certain embodiments, the composition comprises at least 50% enantiomeric excess of the S stereoisomer of the compound of formula (I). In some embodiments, the composition comprises at least 75% enantiomeric excess of the S stereoisomer of the compound of formula (I). In some embodiments, the composition comprises at least 85% enantiomeric excess of the S stereoisomer of the compound of formula (I). In some embodiments, the composition comprises at least 90% enantiomeric excess of the S stereoisomer of the compound of formula (I). In some embodiments, the composition comprises at least 95% enantiomeric excess of the S stereoisomer of the compound of formula (I). In some embodiments, the composition comprises at least 97% enantiomeric excess of the S stereoisomer of the compound of formula (I). In some embodiments, the composition comprises at least 99% enantiomeric excess of the S stereoisomer of the compound of formula (I).

In certain embodiments, the compound of formula (I) is represented by the following formula:

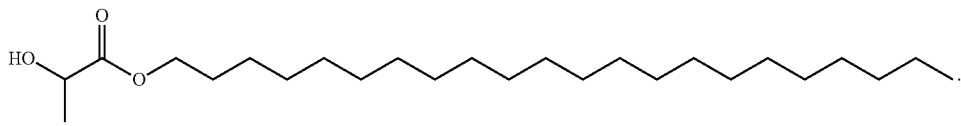 [SMILES: CCCCCCCCCCCCCCCCCCCCCCOC(=O)C(C)O]

In some embodiments, the compound of formula (I) is represented by the following formula:

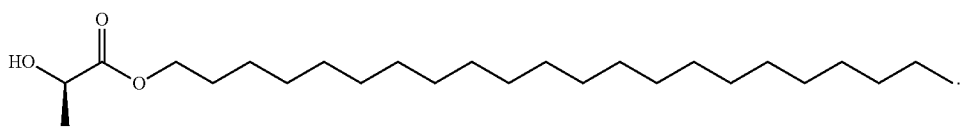 [SMILES: CCCCCCCCCCCCCCCCCCCCCCOC(=O)[C@@H](C)O]

In some embodiments, the compound of formula (I) is represented by the following formula:

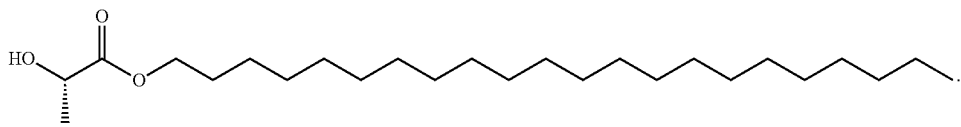 [SMILES: CCCCCCCCCCCCCCCCCCCCCCOC(=O)[C@H](C)O]

In certain embodiments, the composition is in the form of an oil-in-water emulsion. In some embodiments, the composition is in the form of a water-in-oil emulsion. In some embodiments, the composition is in the form of a thickened aqueous gel. In some embodiments, the composition is in the form of a hydrophilic gel. In some embodiments, the composition is in the form of a capsule. In some embodiments, the composition is in the form of a tablet. In some embodiments, the composition is in the form of a hydrophobic ointment. In some embodiments, the composition is in the form of a hydrophilic ointment. In some embodiment, the composition is in the form of an anhydrous gel. In some embodiments, the composition is in the form of a solution.

In certain embodiments, the composition is configured for topical administration. In some embodiments, the composition is configured for oral administration. In some embodiments, the composition is configured for administration in the form of a patch (e.g., the composition is applied to a mounting that can be adhered to the skin of a subject).

In another aspect, the present invention is directed to a method of treating a viral infection, the method comprising administering a compound of formula (I) or composition as described herein.

In certain embodiments, the composition is administered topically. In some embodiments, the composition is administered via a patch.

In certain embodiments, the method comprises administering a compound of formula (I) or composition as described herein once daily. In some embodiments, the method comprises administering a compound of formula (I) or composition as described herein twice daily. In some embodiments, the method comprises administering a compound of formula (I) or composition as described herein three times daily. In some embodiments, the method comprises administering a compound of formula (I) or composition as described herein four times daily. In some embodiments, the method comprises administering a compound of formula (I) or composition as described herein five times daily. In certain embodiments, the method comprises administering a compound of formula (I) or composition as described herein once weekly. In some embodiments, the method comprises administering a compound of formula (I) or composition as described herein once monthly.

In certain embodiments, the viral infection is a herpes viral infection (e.g., a viral infection of Herpes Simplex I, Herpes Simplex II, Herpes Simplex VI, herpes zoster, poxviruses, corona viruses, paramyxoviruses and togaviruses).

In certain embodiments, the method includes a composition including a compound is represented by the following formula:

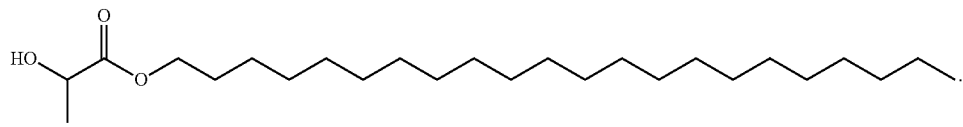 [SMILES: CCCCCCCCCCCCCCCCCCCCCCOC(=O)C(C)O]

In certain embodiments, the method includes a composition including a compound is represented by the following formula:

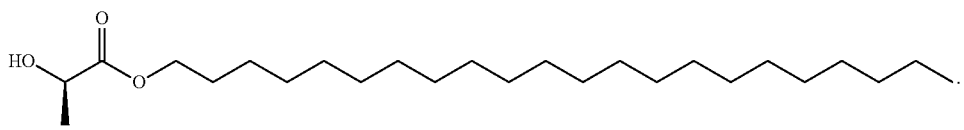 [SMILES: CCCCCCCCCCCCCCCCCCCCCCOC(=O)[C@@H](C)O]

In certain embodiments, the method includes a composition including a compound is represented by the following formula:

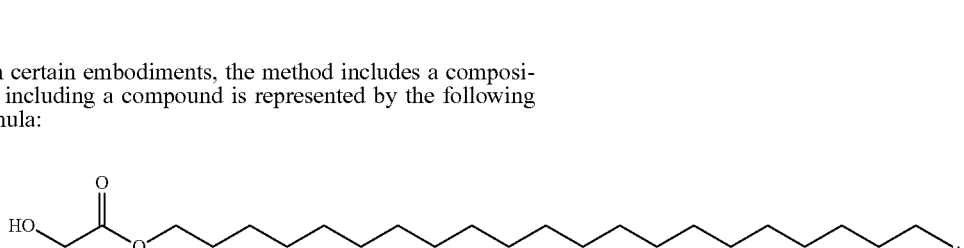

In certain embodiments, the viral infection is on mammalian tissue (e.g., the skin, mucosal tissue or in a wound).

In another aspect, the present invention is directed to a method of treating an inflammatory disease, the method comprising administering a composition as described herein.

In certain embodiments, the composition is administered topically. In some embodiments, the composition is administered intrathecally. In some embodiments, the composition is administered via a patch. In some embodiments, the composition is administered orally.

In certain embodiments, the inflammatory disease is eczema, shingles psoriasis, atopic dermatitis or is an inflammation resulting from a burn, laceration or acute injury.

In certain embodiments, a compound employed in the composition of the above method is represented by the following formula:

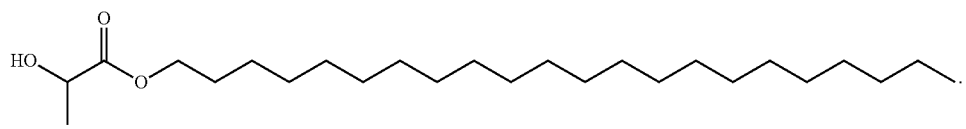 [SMILES: CCCCCCCCCCCCCCCCCCCCCCOC(=O)C(C)O]

In certain embodiments, a compound employed in the composition of the above method is represented by the following formula:

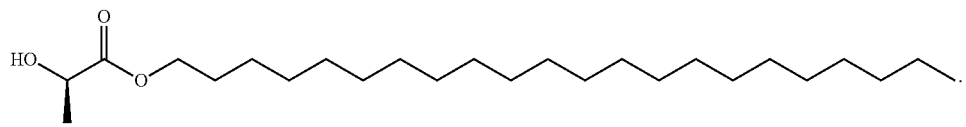 [SMILES: CCCCCCCCCCCCCCCCCCCCCCOC(=O)[C@@H](C)O]

In certain embodiments, a compound employed in the composition of the above method is represented by the following formula:

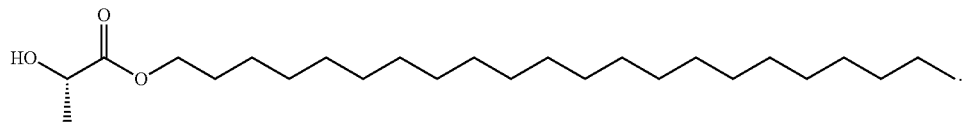 [SMILES: CCCCCCCCCCCCCCCCCCCCCCOC(=O)[C@H](C)O]

In another aspect, the present invention is directed to a method of treating lesions, the method comprising administering a composition as described above.

In certain embodiments, the lesions are caused by a viral infection. In some embodiments, the lesions are cold sores caused by a viral infection. In some embodiments, the lesions are caused by an inflammatory disease.

In certain embodiments, a compound employed in the composition of the above method is represented by the following formula:

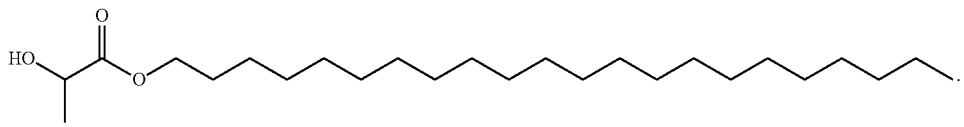 [SMILES: CCCCCCCCCCCCCCCCCCCCCCOC(=O)C(C)O]

In certain embodiments, a compound employed in the composition of the above method is represented by the following formula:

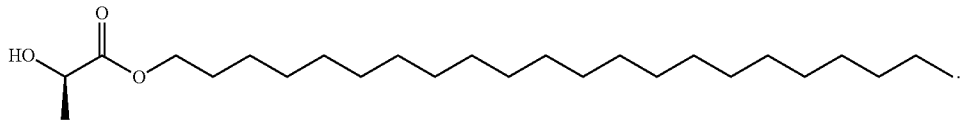 [SMILES: CCCCCCCCCCCCCCCCCCCCCCOC(=O)[C@@H](C)O]

In certain embodiments, a compound employed in the composition of the above method is represented by the following formula:

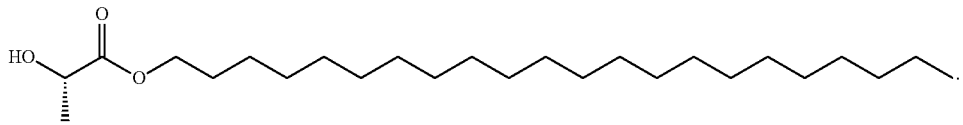

In another aspect, the present invention is directed to a method of making a compound of formula (I), the method comprising reacting a saturated alcohol having a chain length of $C_{15}$-$C_{40}$ with an α-hydroxy ester in the presence of enzymatic conditions in greater than 60% purity.

In certain embodiments, the method of making a compound of formula (I) is carried out in an open reaction vessel.

In certain embodiments, the method includes removing one of the products of the method. In some embodiments, the product is an alcohol. In certain embodiments, the product is an alcohol by-product. In some embodiments, the product is removed by using at least one of the following: evaporation under ambient conditions, evaporation facilitated by heat, rotary evaporation, convection, inert gas flow, application of vacuum, vacuum filtration, distillation, azeotropic distillation, vacuum distillation, chemical modification, enzymatic modification and adsorption. In some embodiments, the adsorption is carried out using molecular sieves.

In certain embodiments, the reaction is carried out on at least 50 g of the saturated alcohol starting material. In some embodiments, the reaction is carried out on at least 100 g of the saturated alcohol starting material. In some embodiments, the reaction is carried out on at least 200 g of the saturated alcohol starting material. In some embodiments, the reaction is carried out on at least 250 g of the saturated alcohol starting material. In some embodiments, the reaction is carried out on at least 400 g of the saturated alcohol starting material. In some embodiments, the reaction is carried out on at least 500 g of the saturated alcohol starting material.

In certain embodiments, the method comprises a batch process of producing a compound of formula (I).

In certain embodiments, the saturated alcohol has a chain length of $C_{15}$-$C_{26}$. In some embodiments, the saturated alcohol has a chain length of $C_{20}$-$C_{26}$. In some embodiments, the saturated alcohol has a chain length of $C_{20}$-$C_{22}$. In some embodiments, the saturated alcohol has a chain length of $C_{22}$.

In certain embodiments, the desired compound is produced in greater than 60% purity in the absence of a purification step. In some embodiments, the desired compound is produced in greater than 70% purity. In some embodiments, the desired compound is produced in greater than 70% purity in the absence of a purification step. In some embodiments, the desired compound is produced in greater than 80% purity. In some embodiments, the desired compound is produced in greater than 80% purity in the absence of a purification step. In some embodiments, the desired compound is produced in greater than 90% purity. In some embodiments, the desired compound is produced in greater than 90% purity in the absence of a purification step. In some embodiments, the desired compound is produced in greater than 95% purity. In some embodiments, the desired compound is produced in greater than 95% purity in the absence of a purification step. In some embodiments, the desired compound is produced in the absence of a purification step.

In certain embodiments, the saturated alcohol is behenyl alcohol. In some embodiments, the α-hydroxy ester is ethyl lactate. In some embodiments, the ethyl lactate is substantially the R stereoisomer. In some embodiments, the ethyl lactate is substantially the S stereoisomer. In some embodiments, the enzyme is a lipase enzyme. In some embodiments, the lipase enzyme is Novozym 435®.

In another aspect, the present invention is directed to a method of making a compound of formula (I), the method comprising reacting a saturated alcohol with an α-hydroxy ester in the presence of enzymatic conditions in greater than 60% yield.

In certain embodiments, the desired compound is produced in greater than 70% yield. In some embodiments, the desired compound is produced in greater than 80% yield. In some embodiments, the desired compound is produced in greater than 90% yield. In some embodiments, the desired compound is produced in greater than 95% yield.

In certain embodiments, the saturated alcohol is behenyl alcohol. In some embodiments, the α-hydroxy ester is ethyl lactate. In some embodiments, the ethyl lactate is substantially the R stereoisomer. In some embodiments, the ethyl lactate is substantially the S stereoisomer.

DEFINITIONS

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "halo" or "halogen" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 carbon atoms in it. The term "haloalkyl" refers to an alkyl in which one or more hydrogen atoms are replaced by halo, and includes alkyl moieties in which all hydrogens have been replaced by halo, e.g., perfluoroalkyl. The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "alkylene" refers to a divalent alkyl, e.g., —CH$_2$—, —CH$_2$CH$_2$—, and —CH$_2$CH$_2$CH$_2$—.

The term "alkenyl" refers to a straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. The term "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The term "aryl" refers to an aromatic monocyclic, bicyclic, or tricyclic hydrocarbon ring system, wherein any ring atom capable of substitution can be substituted, e.g., by one or more substituents. Examples of aryl moieties include, but are not limited to, phenyl, naphthyl, and anthracenyl.

The term "arylalkyl" or the term "aralkyl" refers to alkyl substituted with an aryl. Exemplary aralkyls include but are not limited to benzyl and phenethyl.

The term "cold sore" refers to a small sore situated on the face (e.g., on the lips, chin, cheeks or nostrils) or in the mouth (e.g., the gums or roof of the mouth) that causes pain, burning, or itching before bursting and crusting over. Cold sores, also commonly referred to as fever blisters, are caused by herpes simplex virus type 1. Cold sores (fever blisters) are also referred to as labial herpes (in Latin, herpes labialis) and febrile herpes (herpes febrilis).

The term "cycloalkyl" as employed herein includes saturated cyclic, bicyclic, tricyclic or polycyclic hydrocarbon groups having 3 to 12 carbons. Any ring atom can be substituted, e.g., by one or more substituents. The cycloalkyl groups can contain fused rings. Fused rings are rings that share a common carbon atom. Examples of cycloalkyl moieties include, but are not limited to, cyclopropyl, cyclohexyl, methylcyclohexyl, adamantyl, and norbornyl.

The term "emollient" is a hydrophobic material that provides softness, lubricity and smoothness to the skin and often forms a thin occlusive film which increases hydration by reducing transepidermal water loss (TEWL).

The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer.

$$ee=(90-10)/100=80\%.$$

Thus, a composition containing 90% of one enantiomer and 10% of the other enantiomer is said to have an enantiomeric excess of 80%. Some of the compositions described herein contain an enantiomeric excess of at least 50%, 75%, 90%, 95%, or 99% of Compound 1 (the S-enantiomer). In other words the compositions contain an enantiomeric excess of the S enantiomer over the R enantiomer.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, Si, P or S, e.g., carbon atoms and 1-3, 1-6, or 1-9 heteroatoms of N, O, Si, P or S if monocyclic, bicyclic, or tricyclic, respectively. The heteroatom may optionally be the point of attachment of the heterocyclyl substituent. Any ring atom can be substituted, e.g., by one or more substituents. The heterocyclyl groups can contain fused rings. Fused rings are rings that share a common carbon atom. Examples of heterocyclyl include, but are not limited to, tetrahydrofuranyl, tetrahydropyranyl, piperidinyl, morpholino, pyrrolinyl, pyrimidinyl, quinolinyl, and pyrrolidinyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, Si, P or S, e.g., carbon atoms and 1-3, 1-6, or 1-9 heteroatoms of N, O, Si, P or S if monocyclic, bicyclic, or tricyclic, respectively. Any ring atom can be substituted, e.g., by one or more substituents.

The term "humectant" is a polar hygroscopic material that increases hydration by drawing water from the environment to help retain water in the skin's upper layers.

The term "lesion" refers to an abnormal condition of a tissue (e.g., skin and/or mucous membrane) caused by a microbial (e.g., bacterial, viral and/or fungal) infection.

The term "moisturizer" refers to a material that will increase the level of hydration of skin, mucous membrane, wound, lesion or scab.

The term "substantially free" when referring to a compound or composition described herein means that there is less than 20% (by weight) of the designated compound or by-product (e.g., a saturated alcohol starting material) present, more preferably, there is less than 10% (by weight) of the designated compound or by-product, more preferably, there is less than 9% (by weight) of the designated compound or by-product, more preferably, there is less than 8% (by weight) of the designated compound or by-product, more preferably, there is less than 7% (by weight) of the designated compound or by-product, more preferably, there is less than 6% (by weight) of the designated compound or by-product, more preferably, there is less than 5% (by weight) of the designated compound or by-product, more preferably, there is less than 4% (by weight) of the designated compound or by-product, more preferably, there is less than 3% (by weight) of the designated compound or by-product, more preferably, there is less than 2% (by weight) of the designated compound or by-product, and most preferably, there is less than 1% (by weight) of the designated compound or by-product.

The term "substituents" refers to a group "attached" to a alkyl, cycloalkyl, alkenyl, alkynyl, heterocyclyl, heterocloalkenyl, cycloalkenyl, aryl, or heteroaryl group at any atom of that group. Suitable substituents include, without limitation, alkyl, e.g., C1, C2, C3, C4, C5, C6, C7, C8, C9, C10, C11, C12 straight or branched chain alkyl, cycloalkyl, haloalkyl, e.g., perfluoroalkyl such as $CF_3$, aryl, heteroaryl, aralkyl, heteroaralkyl, heterocyclyl, alkenyl, alkynyl, cycloalkenyl, heterocycloalkenyl, alkoxy, haloalkoxy, e.g., perfluoroalkoxy such as $OCF_3$, halo, hydroxy, carboxy, carboxylate, cyano, nitro, amino, alkyl amino, $SO_3H$, sulfate, phosphate, methylenedioxy e.g., —O—$CH_2$—O—, ethylenedioxy, oxo, thioxo, e.g., C=S, imino, e.g., alkyl, aryl, aralkyl, $S(O)_n$alkyl, $S(O)_n$ aryl, $S(O)_n$ heteroaryl, $S(O)_n$ heterocyclyl, i.e., wherein n is an integer between 0 and 2, amine, e.g., mono-, di-, alkyl, cycloalkyl, aralkyl, heteroaralkyl, aryl, heteroaryl, and combinations thereof, ester, e.g., alkyl, aralkyl, heteroaralkyl, aryl, heteroaryl, amide, e.g., mono-, di-, alkyl, aralkyl, heteroaralkyl, aryl, heteroaryl, and combinations thereof, sulfonamide, e.g., mono-, di-, alkyl, aralkyl, heteroaralkyl, and combinations thereof. In one aspect, the substituents on a group are independently any one single, or any subset of the aforementioned substituents. In another aspect, a substituent may itself be substituted with any one of the above substituents.

The term "wound" refers to an injury to a subject which involves a break in the normal skin or mucosal tissue barrier exposing tissue below, which is caused by, for example, lacerations, surgery, burns, damage to underlying tissue such as pressure sores, poor circulation and the like. Wounds are understood to include both acute and chronic wounds.

DETAILED DESCRIPTION

Compounds

In general, the compounds utilized in the composition of the present application are represented by formula (I):

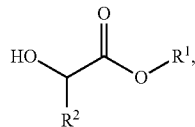

(I)

wherein $R^1$ and $R^2$ are as represented herein.

In one aspect, the invention features a composition containing an enantiomeric excess (ee) of the compound of Formula (I). For example, the composition can contain an ee of at least 50%, 75%, 90%, 95%, or 99%.

A compound described herein can also be in the form of a prodrug. Prodrugs of the compounds described herein are those compounds that readily undergo chemical changes under physiological conditions to provide the compounds of the present invention. In another exemplary embodiment, the prodrug is suitable for treatment/prevention of those diseases and conditions that require the drug molecule to cross the blood brain barrier. In a preferred embodiment, the prodrug enters the brain, where it is converted into the active form of the drug molecule. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

A compound of the present invention can exist in an unsolvated form as well as a solvated form, including hydrated forms. In general, the solvated forms are equivalent to unsolvated forms and are encompassed within the scope of the present invention. Certain compounds of the present invention may exist in multiple crystalline or amorphous forms termed polymorphic forms. In general, all physical forms are of use in the methods contemplated by the present invention and are intended to be within the scope of the present invention. "Compound or a pharmaceutically acceptable salt, hydrate, polymorph or solvate of a compound" intends the inclusive meaning of "or", in that materials meeting more than one of the stated criteria included, for example, a material that is both a salt and a solvate is encompassed.

A compound described herein can be in the form of a metabolite. A metabolite may be a compound that is related to a compound described herein, as a form of such compound obtained in a human or animal body by action of the body on the administered form of the compound. For example, a metabolite may be a de-methylated analogue of a compound bearing a methyl group, which is obtained in the body after administration of the methylated compound as a result of action by the body on the methylated compound. A metabolite may also be a carboxylic-acid containing compound, which is obtained in the body after administration of the corresponding ester as a result of action by the body on the ester-containing compound.

Compositions of the Invention

The present invention features pharmaceutical compositions including any of the compounds described herein, either alone or in combination with one or more excipients. In some embodiments, the pharmaceutical composition is a composition that can be administered topically. In some embodiments, the pharmaceutical composition is a composition that can be administered to a subject orally. In some embodiments, the composition is a composition that can be administered bucally, vaginally, mucosally, nasally (e.g., intranasally) or parenterally, e.g., a liquid composition such as a solution, intranasally or via patch. In some embodiments, the composition is a solid composition, for example, a lyophilisate, which can be further processed prior to administering the composition to a subject, for example, the solid composition can be further processed to form a liquid composition such as a solution.

The compositions described herein, e.g., a composition including a compound of formula (I), can be used as an antiviral, antibacterial and/or antifungal composition. These compositions may also include one or more organoleptic neutralizing agents comprising compounds such as terpineols, alpha-pinene, borneol, borneol acetate, patchoulol, cineol, linalool, citronellal and forskolin. In some embodiments, the compositions described herein consist essentially of a compound of formula (I). Certain compositions may also include one or more external analgesics and/or one or more moisturizers.

The compositions described herein, e.g., a composition including a compound of formula (I), may be used for treating or preventing an infection caused by a herpes virus. The compositions are useful for treating topical skin infections caused by a herpes virus including but not limited to cold sores, shingles and genital herpes (optionally in the form of a topical cream or ointment). The compositions are useful for treating or preventing cold sores caused by the herpes simplex I virus. The compositions are also useful for treating shingles caused by the herpes zoster virus. Certain compositions described herein adhere well to bodily tissues (e.g., mammalian tissues such as skin and mucosal tissues) and thus are very effective topically. Certain methods involve topical application, particularly to skin (e.g., skin lesions) and mucous membranes in and surrounding the oral cavity.

Compositions of the present invention can be used to provide effective topical antimicrobial activity and thereby treat and/or prevent a wide variety of afflictions. For example, they can be used in the treatment and/or prevention of afflictions caused or aggravated by, microorganisms (e.g., gram positive bacteria, gram negative bacteria, fungi, protozoa, mycoplasma, yeast, viruses, and even lipid-enveloped viruses) on skin and/or mucous membranes, such as those in the nose, outer ear, middle ear, mouth, rectum, vagina, or other similar tissues. Organisms that may cause or aggravate such afflictions include viruses of the herpes family; e.g., Herpes Simples I, Herpes Simplex II, Herpes Simplex VI; herpes zoster, poxvirus, corona virus, paramyxovirus and togavirus.

Exemplary compositions may include one or more additional excipients. Said excipients may be selected from, but not limited to moisturizers, skin protectants, enhancer components, surfactants, and thickeners.

Moisturizers

Compositions of the present invention may include a moisturizer to increase the level of hydration of the skin, mucous membrane, wound, lesion or scab. The moisturizer can be a hydrophilic material including humectants or it can be a hydrophobic material including emollients. A humectant is a polar hygroscopic material that increases hydration by drawing water from the environment to help retain water in the skin's upper layers. An emollient is a hydrophobic material that provides softness, lubricity and smoothness to the skin and often forms a thin occlusive film that increases hydration by reducing transepidermal water loss (TEWL). Exemplary hydrophilic moisturizers include, but are not limited to, water, polyhydric alcohols, lower alkyl ethers, N-methylpyrrolidone, lower alkyl esters, urea, amino acids, ethoxylated amides, sodium pyrrolidone carboxylic acid, and the lower monohydroxy alcohols and hydroxy acids discussed below as enhancers, as well as combinations thereof. Thus, a lower monohydroxy alcohol can function as both a hydrophilic compound and an enhancer. Preferably, the hydrophilic components include polyhydric alcohols, lower alkyl ethers, and short chain esters. More preferably, the hydrophilic components include polyhydric alcohols.

Exemplary hydrophobic moisturizers include, but are not limited to, short chain (i.e., C1-C6) alkyl or (C6-C12) aryl esters of long (i.e., C8-C36) straight or branched chain alkyl or alkenyl alcohols or acids and polyethoxylated derivatives of the alcohols; short chain (i.e., C1-C6) alkyl or (C6-C12) aryl esters of (C4-C12) diacids or (C4-C12) diols optionally substituted in available positions by —OH; (C2-C18) alkyl or (C6-C12) aryl esters of glycerol, pentaerythritol, ethylene glycol, propylene glycol, as well as polyethoxylated derivatives of these; (C12-C22) alkyl esters or (C12-C22) ethers of polypropylene glycol; (C12-C22) alkyl esters or (C12-C22) ethers of polypropylene glycol/polyethylene glycol copolymer; and polyether polysiloxane copolymers. Additional examples of hydrophobic components include cyclic dimethicones, including volatile cyclic silicones such as D4 and D5, polydialkylsiloxanes, polyaryl/alkylsiloxanes, silicone copolyols, cocoa butter, beeswax, jojoba oil, lanolin and derivatives, long chain (i.e., C8-C36) alkyl and alkenyl esters of long (i.e., C8-C18) straight or branched chain alkyl or alkenyl alcohols or acids, long chain (i.e., C8-C36) alkyl and alkenyl amides of long straight or branched chain (i.e., C8-C36) alkyl or alkenyl amines or acids; hydrocarbons including straight and branched chain alkanes and alkenes such as isoparafins (e.g., isooctane, isododecane, isooctadecane, etc.), squalene, and mineral oil, polysiloxane polyalkylene copolymers, dialkoxy dimethyl polysiloxanes; (C12-C22) alkyl and (C12-C22) alkenyl alcohols, and petroleum derived alkanes such as isoparafins, petrolatum, petrolatum USP, as well as refined natural oils (especially NF or USP grades) such as olive oil NF, cotton seed oil, castor oil, peanut oil, corn oil, seasame oil, safflower oil, soybean oil, sunflower oil and the like, and blends thereof. In certain preferred embodiments, the hydrophobic components useful in the compositions of the present invention include those selected from the group consisting of petrolatum USP and short chain (i.e., C1-C6) alkyl or (C6-C12) aryl esters of long (i.e., C8-C36) straight or branched chain alkyl or alkenyl alcohols or acids and polyethoxylated derivatives of the alcohols; short chain (i.e., C1-C6) alkyl or (C6-C12) aryl esters of (C4-C12) diacids or (C4-C12) diols optionally substituted in available positions by —OH (such as diisopropyladipate, diisopropylsebacate); (C1-C9) alkyl or (C6-C12) aryl esters of glycerol, pentaerythritol, ethylene glycol, propylene glycol (such as glyceryl tricaprylate/caprate); and mixtures thereof.

Skin Protectants

Compositions of the present invention may also include a skin protectant. Certain materials including some humectants or emollients are also useful at providing safe and effective skin protection. When used in the appropriate amount they temporarily protect injured or exposed skin or mucous membrane surfaces from harmful stimuli and may help provide relief to such surfaces. Similarly, sunscreens may be included, which protect the skin from harmful ultraviolet radiation. Information concerning safe and effective skin protectants is provided in the Proposed Final Rulemaking for Fever Blister and Cold Sore Treatment Drug Products in the Skin Protectant Drug Products for Over-the-counter Human Use Monograph, published by the United States Food and Drug Administration in the Federal Register, Volume 51, Number 21, Jan. 31, 1990, pages 3362 to 3370.

Enhancer Component

Compositions of the present invention may optionally include an enhancer to enhance the antimicrobial activity (e.g., against gram negative bacteria). The enhancer component may include but is not limited to an alpha-hydroxy acid, a beta-hydroxy acid, other carboxylic acids, a (C1-C4) alkyl carboxylic acid, a (C6-C12) aryl carboxylic acid, a (C6-C12) aralkyl carboxylic acid, a (C6-C12) alkaryl carboxylic acid, a phenolic compound (such as certain antioxidants and parabens), a (C1-C10) monohydroxy alcohol, a chelating agent, or a glycol ether (i.e., ether glycol) and/or mixtures thereof.

Surfactants

Compositions of the present invention optionally may include one or more surfactants to emulsify the composition and to help wet the surface and/or to aid in contacting the microorganisms. In general, a "surfactant" refers to an amphiphile (i.e., a molecule possessing both polar and non-polar regions which are covalently bound) capable of reducing the surface tension of water and/or interfacial tension between water and an immiscible liquid. Surfactants that may be employed in the present compositions include, but are not limited to include soaps, detergents, emulsifiers, surface active agents, and the like. The surfactant can be cationic, anionic, nonionic, or amphoteric. In preferred embodiments, the surfactant includes poloxamer, ethoxylated stearates, sorbitan oleates, high molecular weight crosslinked copolymers of acrylic acid and a hydrophobic comonomer, and cetyl and stearyl alcohols as cosurfactants.

Thickeners

Compositions of the present invention may also include thickeners that are soluble, swellable, or insoluble organic polymeric thickeners such as natural and synthetic polymers including polyacrylic acids, poly(N-vinyl pyrrolidones), cellulosic derivatives, silicone elastomers and xanthan or guar gums or inorganic thickeners such as silica, fumed silica, precipitated silica, silica aerogel and carbon black, and the like; other particle fillers such as calcium carbonate, magnesium carbonate, kaolin, talc, titanium dioxide, aluminum silicate, diatomaceous earth, ferric oxide and zinc oxide, clays, and the like; ceramic microspheres or glass microbubbles; ceramic microspheres such as those available under the tradenames "ZEOSPHERES" or "Z-LIGHT" from 3M Company, St. Paul, Minn. and/or combinations thereof.

Forms

The pharmaceutical compositions of this invention may be administered orally. Compositions suitable for oral administration may be in the form of capsules, cachets, pills, tablets, lozenges (using a flavored base, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention(s) as an active ingredient.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain pacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

In addition, the compositions described herein may be administered topically, transdermally, rectally, vaginally, parentally, intranasally, intrapulmonary, intraocularly, intravenously, intramuscularly, intraarterially, intrathecally, intracapsularly, intraorbitally, intracardiacly, intradermally, intraperitoneally, transtracheally, subcutaneously, subcuticularly, intraarticularly, subcapsularly, subarachnoidly, intraspinally, intrasternally or by inhalation.

Generally, the compositions of this invention may also be in one of the following forms:

A hydrophobic or hydrophilic ointment wherein the composition is formulated with a hydrophobic base (e.g., petroleum, thickened or gelled water-insoluble oils, etc.) and optionally having a minor amount of a water soluble phase. Hydrophilic ointments generally contain one or more surfactants or wetting agents.

An oil-in-water emulsion wherein the compositions described may be formulated in which the antiviral component is emulsified into an emulsion comprising a discrete phase of a hydrophobic component and a continuous aqueous phase that includes water and optionally one or more polar hydrophilic material(s) as well as salts, surfactants, emulsifiers and other components. These emulsions may include water soluble or water-swellable polymers as well as one or more emulsifiers that help to stabilize the emulsion. These emulsions generally have higher conductivity values, as disclosed in U.S. Pat. No. 7,030,203.

A water-in-oil emulsion wherein the compositions described herein may be formulated so that the antiviral components are incorporated into an emulsion that includes a continuous phase of a hydrophobic component and an aqueous phase that includes water and optionally one or more polar hydrophilic material(s) as well as salts or other components. These emulsions may include oil-soluble or oil-swellable polymers as well as one or more emulsifier(s) that help to stabilize the emulsion.

Thickened aqueous gels refer to systems including an aqueous phase which has been thickened by suitable natural, modified natural or synthetic polymers as described herein. Alternatively, the thickened aqueous gels can be thickened using suitable polyethoxylated alkyl chain surfactants that effectively thicken the composition as well as other non-ionic, cationic or anionic emulsifier systems.

Hydrophilic gels refer to systems in which the continuous phase includes at least one water soluble or water dispersible hydrophilic component other than water. The formulations may optionally also contain water up to 20% by weight. Higher levels may be suitable in some compositions. Suitable hydrophilic components include one or more glycols such as polyols such as glycerin, propylene glycol, butylene glycols, polyethylene glycols (PEGS), random or block copolymers of ethylene oxide, propylene oxide, and/or butylene oxide, polyalkoxylated surfactants having one or more hydrophobic moieties per molecule, silicone copolyols, as well as combinations thereof. One of ordinary skill in the art will recognize and understand that the level of ethoxylation should be sufficient to render the hydrophilic component water soluble or water dispersible at 23° C. In most embodiments, the water content is less than 20%, preferably less than 10% and preferably less than 5% by weight of the composition.

Methods of Making Compounds as Described Herein

The compounds employed in the compositions described herein (e.g., a compound of formula I) can be made using a variety of synthetic techniques.

Scheme 1
Scheme 1. Enzymatic synthesis of lactate esters

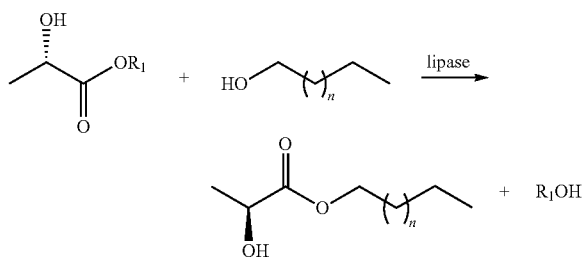

As can be appreciated by the skilled artisan, methods of synthesizing the compounds of the formulae herein will be evident to those of ordinary skill in the art. Additionally, any synthetic steps described herein may be performed in an alternate sequence or order to give the desired compounds. Synthetic chemistry transformations and protecting group methodologies, i.e., protection and deprotection, useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Reaction Mixtures

The present invention refers to compositions comprising a compound as described herein, including a reaction mixture, e.g., a reaction mixture that is present during a method or process described herein.

In certain embodiments, the methods described herein further comprise a solvent. In certain embodiments, the solvent is an organic solvent. In certain embodiments, the solvent is an aprotic solvent. Exemplary organic solvents include, but are not limited to, benzene, toluene, xylenes, acetonitrile, acetone, ethyl ether, tetrahydrofuran, methylene chloride, dichloroethane and chloroform, or a mixture thereof. In certain embodiments, the solvent is acetonitrile. In certain embodiments, the solvent is methylene chloride. In certain embodiments, the solvent is tetrahydrofuran. In certain embodiments, the solvent is dichloroethane. In certain embodiments, the solvent is benzene.

In certain embodiments, the reaction is a reaction below room temperature, e.g., a cooled reaction such as a reaction at a temperature of 0° C. or lower. In certain embodiments, the reaction is a heated reaction, e.g., a reaction occurring above room temperature. In certain embodiments, the reaction is a reaction run at room temperature. In certain embodiments, the reaction occurs under an inert atmosphere, e.g, an atmosphere of an inert gas such as nitrogen or argon. In certain embodiments, the reaction takes place under anhydrous conditions, e.g., conditions that are substantially free of water.

Described herein are compositions comprising a compound described herein, e.g., a compound of formula (I). In some embodiments, the compounds described herein are in a composition comprising a solvent, e.g., as a mixture such as a solution or a heterogeneous mixture. The composition can be free of compounds that would react with or degrade a compound described herein e.g., the composition can be substantially free of water and/or substantially free of any reactive gases.

EXAMPLES

Example 1

Synthesis of Docosyl Lactate

Ethyl lactate (30 mL, 3.0 eq.) was added to a 100 mL jacketed beaker. The jacket of the beaker was connected to a circulating water bath (set point=60° C.), and 1-docosanol (28.7 g, 1.0 eq.) was added to the beaker. Enzyme (7.75 g; lipase B from *Candida Antarctica* immobilized on macroporous acrylic resin beads; Novozym® 435) was added to the beaker and the mixture was stirred for 24 h (IKA RW16 Basic).

Dichloromethane (20 mL) was added to the hot mixture, which was then vacuum filtered (Whatman Grade 1). The enzyme was washed with dichloromethane (230 mL), and the combined filtrates were concentrated in vacuo to give a wax-like solid. The solid was taken up in fresh dichloromethane (~250 mL) and diluted with hexanes (~125 mL). Concentration gave a granular waxy solid. Yield: 27.1 g; purity (GC): ~94%; mp 55-56.3° C.

Example 2

Formulations Comprising Docosyl Lactate

General Preparation Procedure

All components were weighed into a 40 mL clear glass vial, which was then placed in a hot oil bath ($T_{bath}$=90±10° C.). The mixture was stirred with a spatula as it was heated, eventually producing a homogeneous, translucent solution. Stirring was continued as the mixture cooled to RT to provide an opaque cream, which was then homogenized for 1-2 minutes (Ultra-Turrax 25 Basic equipped with a S25N-10G dispersing tool).

A. Topical Cream Gel

| | | % w/w | Trade Name/Supplier |
|---|---|---|---|
| 1. | Cylcopentasiloxane | 40.00 | ST-Cyclomethicone 5-NF/Dow Corning |
| 2. | Docosyl lactate | 10.00 | Chemic Laboratories |
| 3. | Myristyl lactate, 97+% | 10.00 | Chemic Laboratories |
| 4. | Caprylic/capric triglyceride | 10.00 | Labrafac Lipophile WL1349/Gattefosse |
| 5. | Lauryl lactate, 98+% | 5.00 | Chrystaphyl ®/Chemic Laboratories |
| 6. | Octisalate | 5.00 | Spectrum |
| 7. | Cyclopentasiloxane (and) dimethicone crosspolymer | 5.00 | ST-Elastomer 10/Dow Corning |
| 8. | Nylon-611/dimethicone copolymer (and) PPG-3 myristyl ether | 5.00 | 28178 Gellant/Dow Corning |
| 9. | Coco-caprylate/caprate | 3.50 | Cetiol LC ®/Cognis |
| 10. | L-Menthol, USP | 3.00 | Spectrum |
| 11. | *Aloe vera* (aloe) oil extract (and) coconut oil | 2.00 | Concentrated Aloe Corporation |
| 12. | Vitamin E acetate, USP | 1.00 | Spectrum |
| 13. | Vitamin A palmitate, USP | 0.50 | Spectrum |

B. Topical Cream Gel

| | | % w/w | Trade Name/Supplier |
|---|---|---|---|
| 1. | Cylcopentasiloxane | 40.00 | ST-Cyclomethicone 5-NF/Dow Corning |
| 2. | Docosyl lactate | 10.00 | Chemic Laboratories |
| 3. | Myristyl lactate, 95+% | 10.00 | Chemic Laboratories |
| 4. | Caprylic/capric triglyceride | 10.00 | Labrafac Lipophile WL1349/Gattefosse |
| 5. | Lauryl lactate, 97+% | 5.00 | Chrystaphyl ®/Chemic Laboratories |
| 6. | Octisalate | 5.00 | Spectrum |
| 7. | Cydopentasiloxane (and) dimethicone crosspolymer | 5.00 | ST-Elastomer 10/Dow Corning |
| 8. | Nylon-611/dimethicone copolymer (and) PPG-3 myristyl ether | 5.00 | 28178 Gellant/Dow Corning |
| 9. | Coco-caprylate/caprate | 3.50 | Cetiol LC ®/Cognis |
| 10. | $C_{12-15}$ alkyl benzoate | 3.00 | Finsolv TN ®/Innospec |
| 11. | Menthyl lactate | 2.00 | Frescolat ® ML/Symrise 115 |
| 12. | Vitamin E acetate, USP | 1.00 | Spectrum |
| 13. | Vitamin A palmitate, USP | 0.50 | Spectrum |

C. Topical Cream Gel

| | | % w/w | Trade Name/Supplier |
|---|---|---|---|
| 1. | Cylcopentasiloxane | 25.00 | ST-Cyclomethicone 5-NF/Dow Corning |
| 2. | Docosyl lactate | 10.00 | Chemic Laboratories |
| 3. | Myristyl lactate, 95+% | 10.00 | Chemic Laboratories |
| 4. | Caprylic/capric triglyceride | 10.00 | Labrafac Lipophile WL1349/Gattefosse |
| 5. | Coco-caprylate/caprate | 10.00 | Cetiol ® LC/Cognis |
| 6. | Oleyl erucate | 6.00 | Cetiol ® J-600/Cognis |
| 7. | Lauryl lactate, 97+% | 5.00 | Chrystaphyl ®/Chemic Laboratories |
| 8. | Octisalate | 5.00 | Spectrum |
| 9. | Nylon-611/dimethicone copolymer (and) PPG-3 myristyl ether | 5.00 | 28178 Gellant/Dow Corning |
| 10. | $C_{12-15}$ alkyl benzoate | 5.00 | Finsolv TN ®/Innospec |
| 11. | Isostearyl neopentanoate | 5.00 | Crodamol ISNP-LQ-(MH)/Croda |
| 12. | Benzyl alcohol | 2.50 | Aldrich |
| 13. | Vitamin E acetate, USP | 1.00 | Spectrum |
| 14. | Vitamin A palmitate, USP | 0.50 | Spectrum |

D. Topical Cream Gel

| | | % w/w | Trade Name/Supplier |
|---|---|---|---|
| 1. | Dimethicone (and) trisiloxane | 25.00 | 2-1184 Fluid/Dow Corning |
| 2. | Docosyl lactate | 10.00 | Chemic Laboratories |
| 3. | Myristyl lactate, 95+% | 10.00 | Chemic Laboratories |
| 4. | Caprylic/capric triglyceride | 10.00 | Labrafac Lipophile WL1349/Gattefosse |
| 5. | Coco-caprylate/caprate | 10.00 | Cetiol ® LC/Cognis |
| 6. | Oleyl erucate | 6.00 | Cetiol ® J-600/Cognis |
| 7. | Lauryl lactate, 97+% | 5.00 | Chrystaphyl ®/Chemic Laboratories |
| 8. | Octisalate | 5.00 | Spectrum |
| 9. | Nylon-611/dimethicone copolymer (and) PPG-3 myristyl ether | 5.00 | 28178 Gellant/Dow Corning |
| 10. | $C_{12-15}$ alkyl benzoate | 5.00 | Finsolv TN ®/Innospec |
| 11. | Isostearyl neopentanoate | 5.00 | Crodamol ISNP-LQ-(MH)/Croda |
| 12. | Benzyl alcohol | 2.50 | Aldrich |
| 13. | Vitamin E acetate, USP | 1.00 | Spectrum |
| 14. | Vitamin A palmitate, USP | 0.50 | Spectrum |

E. Topical Cream Gel

| | | % w/w | Trade Name/Supplier |
|---|---|---|---|
| 1. | Hexamethyldisiloxane (and) octamethyltrisiloxane | 25.00 | Q7-9180 Silicone Fluid/Dow Corning |
| 2. | Docosyl lactate | 10.00 | Chemic Laboratories |
| 3. | Myristyl lactate, 95+% | 10.00 | Chemic Laboratories |
| 4. | Caprylic/capric triglyceride | 10.00 | Labrafac Lipophile WL1349/Gattefosse |
| 5. | Coco-caprylate/caprate | 10.00 | Cetiol ® LC/Cognis |
| 6. | Oleyl erucate | 6.00 | Cetiol ® J-600/Cognis |
| 7. | Lauryl lactate, 97+% | 5.00 | Chrystaphyl ®/Chemic Laboratories |
| 8. | Octisalate | 5.00 | Spectrum |
| 9. | Nylon-611/dimethicone copolymer (and) PPG-3 myristyl ether | 5.00 | 28178 Gellant/Dow Corning |
| 10. | $C_{12-15}$ alkyl benzoate | 5.00 | Finsolv TN ®/Innospec |
| 11. | Isostearyl neopentanoate | 5.00 | Crodamol ISNP-LQ-(MH)/Croda |
| 12. | Benzyl alcohol | 2.50 | Aldrich |
| 13. | Vitamin E acetate, USP | 1.00 | Spectrum |
| 14. | Vitamin A palmitate, USP | 0.50 | Spectrum |

F. Topical Cream Gel

| | | % w/w | Trade Name/Supplier |
|---|---|---|---|
| 1. | Phenyl trimethicone | 25.00 | 556 Cosmetic Grade Fluid/Dow Corning |
| 2. | Docosyl lactate | 10.00 | Chemic Laboratories |
| 3. | Myristyl lactate, 95+% | 10.00 | Chemic Laboratories |
| 4. | Caprylic/capric triglyceride | 10.00 | Labrafac Lipophile WL1349/Gattefosse |
| 5. | Coco-caprylate/caprate | 10.00 | Cetiol ® LC/Cognis |
| 6. | Oleyl erucate | 6.00 | Cetiol ® J-600/Cognis |
| 7. | Lauryl lactate, 97+% | 5.00 | Chrystaphyl ®/Chemic Laboratories |
| 8. | Octisalate | 5.00 | Spectrum |
| 9. | Nylon-611/dimethicone copolymer (and) PPG-3 myristyl ether | 5.00 | 28178 Gellant/Dow Corning |
| 10. | $C_{12-15}$ alkyl benzoate | 5.00 | Finsolv TN ®/Innospec |
| 11. | Isostearyl neopentanoate | 5.00 | Crodamol ISNP-LQ-(MH)/Croda |
| 12. | Benzyl alcohol | 2.50 | Aldrich |
| 13. | Vitamin E acetate, USP | 1.00 | Spectrum |
| 14. | Vitamin A palmitate, USP | 0.50 | Spectrum |

Michelle K. Lee
*Director of the United States Patent and Trademark Office* with:
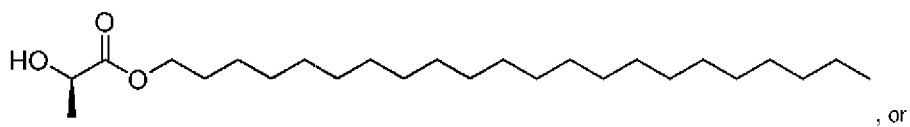, or
In Column 20, lines 37-44, the structure of the represented compound was drawn incorrectly.
Replace:
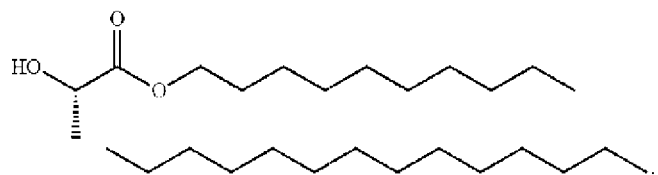
with:
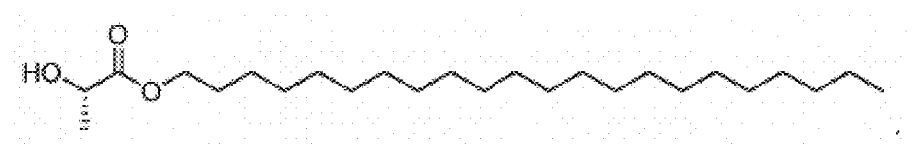

What is claimed is:

1. A method of treating a herpes viral infection, the method comprising administering a composition of a compound represented by the following formula:

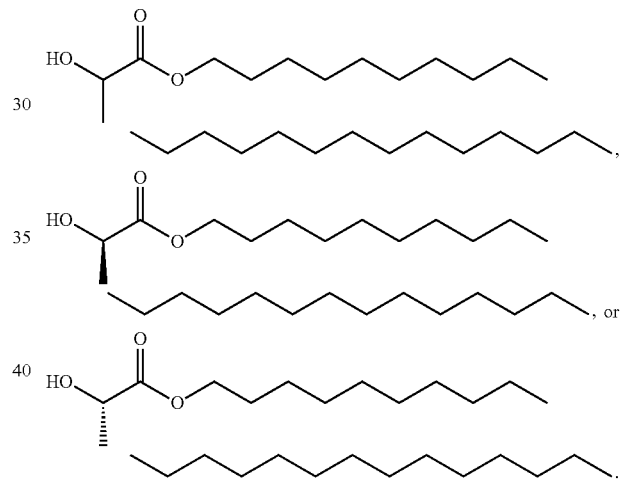

2. The method of claim 1, wherein the composition is administered topically or via a patch.

3. The method of claim 1, wherein the viral infection is on mammalian tissue.

* * * * *

UNITED STATES PATENT AND TRADEMARK OFFICE
CERTIFICATE OF CORRECTION

PATENT NO.         : 9,242,923 B2
APPLICATION NO.    : 13/634170
DATED              : January 26, 2016
INVENTOR(S)        : Joseph P. St. Laurent et al.

It is certified that error appears in the above-identified patent and that said Letters Patent is hereby corrected as shown below:

In The Claims,

In Column 20, lines 26-33, the structure of the represented compound was drawn incorrectly.

Replace:

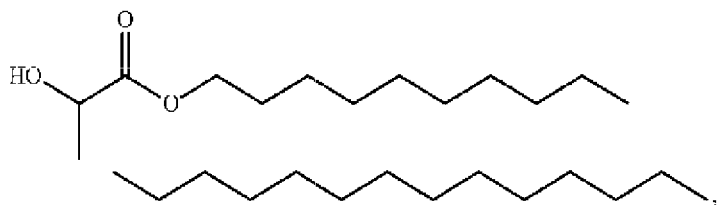

with:

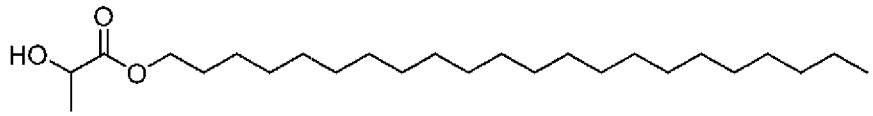

In Column 20, lines 32-39, the structure of the represented compound was drawn incorrectly.

Replace:

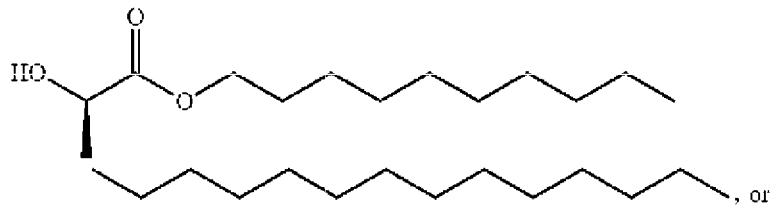

, or

Signed and Sealed this
Fifth Day of July, 2016